(12) United States Patent
Denk et al.

(10) Patent No.: US 9,744,392 B1
(45) Date of Patent: Aug. 29, 2017

(54) COMPOUNDS AND METHODS FOR THE REDUCTION OF HALOGENATED HYDROCARBONS

(71) Applicant: University of Guelph, Guelph (CA)

(72) Inventors: Michael K. Denk, Mississauga (CA);
Nicholas Milutinovic, Oakville (CA);
Katherine Marczenko, Toronto (CA)

(73) Assignee: UNIVERSITY OF GUELPH, Guelph, Ontario (CA)

( * ) Notice: Subject to any disclaimer, the term of this patent is extended or adjusted under 35 U.S.C. 154(b) by 0 days.

(21) Appl. No.: 15/440,077

(22) Filed: Feb. 23, 2017

Related U.S. Application Data

(60) Provisional application No. 62/299,217, filed on Feb. 24, 2016.

(51) Int. Cl.

| | | |
|---|---|---|
| C07C 17/25 | (2006.01) | |
| C07C 17/361 | (2006.01) | |
| C07C 45/00 | (2006.01) | |
| C07C 1/30 | (2006.01) | |
| A62D 3/37 | (2007.01) | |
| A62D 101/22 | (2007.01) | |
| A62D 101/02 | (2007.01) | |
| C22B 3/00 | (2006.01) | |
| B09C 1/08 | (2006.01) | |

(52) U.S. Cl.
CPC .............. *A62D 3/37* (2013.01); *B09C 1/08* (2013.01); *C07C 1/30* (2013.01); *C07C 17/25* (2013.01); *C07C 17/361* (2013.01); *C07C 45/00* (2013.01); *C22B 11/042* (2013.01); *A62D 2101/02* (2013.01); *A62D 2101/22* (2013.01)

(58) Field of Classification Search
CPC ....... C07C 17/25; C07C 17/361; C07C 45/00; C07C 1/30; A62D 3/37; A62D 2101/22; A62D 2101/02; C22B 11/042; B09C 1/08
See application file for complete search history.

(56) References Cited

U.S. PATENT DOCUMENTS 6,649,044 B1 * 11/2003 Bolsing .................... A62D 3/34
208/262.1

OTHER PUBLICATIONS

Denk M. K., Gupta, S., Brownie, J., Tajammul, S., Lough, A. J., "C-H activation with elemental sulfur: synthesis of cyclic thioureas from formaldehyde aminals and S8". Chem. Eur. J. 7, 4477-4486 (2001).
Denk, M. K., Hezarkhani, A., Zheng, F., Steric and Electronic Effects in the Dimerization of Wanzlick Carbenes: The Alkyl Effect. Eur. J. Inorg. Chem. 3527-3534 (2007).
Rabe, E., Wanzlick, H.-W. "Dehydrierung von 1,3-Diaryl-imidazolidinen mit Tetrachlor-kohlenstoff" Liebigs Ann. Chem. 40-44 (1973).
Denk, M.K. et al., "Nature's hydrides: rapid reduction of halocarbons by folate model compounds" Chem. Sci. DOI: 10.1039/c6sc04314c Published Nov. 17, 2016.

* cited by examiner

*Primary Examiner* — Jafar Parsa
(74) *Attorney, Agent, or Firm* — Bereskin & Parr LLP/S.E.N.C.R.L., s.r.l.; Patricia Folkins; Andrea Berenbaum

(57) ABSTRACT

The present application relates to methods for the reduction of halogenated hydrocarbons using compounds of Formula (I):

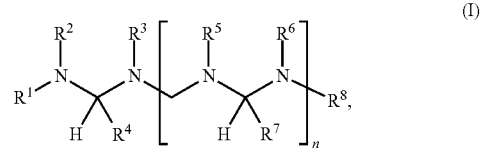

wherein the reduction of the halogenated compounds is carried out, for example, under ambient conditions without the need for a transition metal containing co-factor. The present application also relates to methods of recovering precious metals using compounds of Formula (I) that are absorbed onto a support material.

20 Claims, No Drawings

COMPOUNDS AND METHODS FOR THE REDUCTION OF HALOGENATED HYDROCARBONS

CROSS-REFERENCE TO RELATED APPLICATIONS

The present application claims the benefit of priority from U.S. provisional application No. 62/299,217 filed on Feb. 24, 2016, the contents of which are incorporated herein by reference in their entirety.

FIELD

The present application relates to compounds and methods for the reduction of halogenated hydrocarbons, for example, for the remediation of contaminated environments.

BACKGROUND

Halogenated hydrocarbons such as halomethanes, halogenated ethanes, ethenes and the like are widely used as refrigerants, inhalation narcotics, chemical intermediates and synthetic building blocks, fumigants, pesticides, flame retardants and pharmaceuticals [1]. As a result, these halogenated hydrocarbons have been found to be ubiquitous contaminants in air, water and food, some of which have been shown to be toxic and carcinogenic [2-4]. Further, a small number of halogenated hydrocarbons combine chemical inertness with high toxicity and are problematic as they tend to resist known remediation efforts.

Previously, halogenated hydrocarbons were reduced to hydrocarbons halogenated to a lesser degree under the action of certain metals. For instance, zinc has been used in the reduction of carbon tetrachloride to chloroform [5] and metal bonded hydrogen radicals generated in situ have been used to reduce halogenated hydrocarbons [6].

Only a small number of reagents are capable of reacting with halogenated hydrocarbons under ambient conditions. Unfortunately, many of these reagents, like hydroboranes, silanes and complex hydrides, are highly sensitive to air and moisture or are even hypergolic, toxic, expensive or all of the above. Tin hydrides like $Ph_3Sn$—H, $Bu_3Sn$—H or $Me_3Sn$—H are less sensitive to air and moisture but are highly toxic and thus are not useful to detoxify industrial waste or contaminated soil or water.

SUMMARY

The present application discloses compounds and methods for the reduction of halogenated hydrocarbons, for example, under ambient conditions.

Accordingly, the present application includes a method of reducing one or more halogenated compounds comprising contacting the one or more halogenated compounds with one or more compounds of Formula (I) under conditions for the reduction of the one or more halogenated compounds, wherein the compound of Formula (I) is:

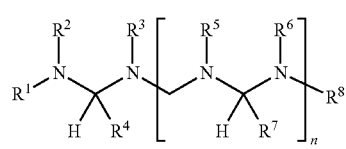

(I)

wherein $R^1$, $R^2$, $R^3$ and $R^8$ and each $R^5$ and $R^6$ are independently selected from $C_{1-6}$alkyl, $C_{3-10}$cycloalkyl, $C_{6-10}$aryl and heteroaryl; or $R^2$ and $R^3$ and/or each $R^5$ and $R^6$, together with the nitrogen atoms to which they are attached, form a 5-7 membered carbocycle wherein 1 or 2 carbons are optionally replaced with $NR^9$;

$R^4$ and each $R^7$ are independently selected from H and $C_{1-6}$alkyl;

each $R^9$ is independently selected from $C_{1-6}$alkyl, $C_{3-10}$cycloalkyl, $C_{6-10}$aryl and heteroaryl; and n is 0-18, and wherein the one or more halogenated compounds, is not $CA_4$, wherein A is chloro.

The present application also includes a method of recovering precious metals, the method comprising:
a) adsorbing one or more compounds of Formula (I) as defined in the embodiments of the application onto a support material;
b) contacting a solution comprising precious metals with the adsorbed one or more compounds of Formula (I) under conditions for the reduction of the precious metals; and
c) removing the adsorbed precious metals from the support material.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The present description refers to a number of chemical terms and abbreviations used by those skilled in the art. Nevertheless, definitions of selected terms are provided for clarity and consistency.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The expression "proceed to a sufficient extent" as used herein with reference to the reactions or process/method steps disclosed herein means that the reactions or process/method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 50%, suitably less than 20%, suitably less than 10%, more suitably less than 5%) of compounds having alternate stereochemistry.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art. Examples of inert solvents include, but are not limited to, benzene, toluene, tetrahydrofuran, acetone, dioxane, hexanes, ethyl ether, ethyl acetate, dimethyl formamide (DMF), acetonitrile, $C_{1-6}$alkyl OH (e.g. methanol, ethanol, 1-propanol, 2-propanol, 1-butanol, butan-2-ol and 2-methyl-1-propanol), diethylcarbonate, hexane and dimethylsulfoxide (DMSO). Further examples can include aqueous solutions, such as water and dilute acids and bases, and ionic liquids, provided that such solvents do not interfere with the reaction.

The term "solvent" includes both a single solvent and a mixture comprising two or more solvents. In some embodiments, the solvent is the halogenated hydrocarbon which is used in excess amounts.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{2-4}$alkylene means an alkylene group having 2, 3 or 4 carbon atoms.

The term "aryl" as used herein, whether it is used alone or as part of another group, refers to cyclic groups that contain at least one aromatic ring. In an embodiment of the application, the aryl group contains from 6, 9 or 10 atoms, such as phenyl, naphthyl or indanyl.

The term "heteroaryl" as used herein refers to cyclic groups that contain at least one aromatic ring and at least one heteroatom, such as N, O and/or S. The term $C_{5-10}$heteroaryl means an aryl group having 5, 6, 7, 8, 9 or 10 atoms, in which at least one atom is a heteroatom, such as N, O and/or S.

The term "cycloalkyl" as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The terms "halogen" or "halogenated" as used herein, whether it is used alone or as part of another group, refers to a halogen atom and includes Cl, Br and I.

The term "carbocycle" as used herein refers to an aromatic or non-aromatic ring wherein each atom comprising the ring is a carbon atom.

The terms "reducing" or "reduction" as used herein refer to the selective replacement of a halogen atom with a hydrogen atom.

The term "reducing agent" as used herein refers to any compound or combination of compounds that reduces a desired functional group. A reducing agent results in the overall addition of electrons, or in the case of organic chemistry, hydrogen atoms to the functional group.

The term "oxidant" as used herein refers to a reagent that provides an oxygen species for participation in the metal catalyzed reactions of the present application. In an embodiment, the oxygen source is $O_2$ gas, air or an inorganic or organic peroxide (i.e. a compound comprising an "O—O" functionality).

The term "counteranion" as used herein refers to a negatively charged species consisting of a single element, or a negatively charged species consisting of a group of elements connected by ionic and/or covalent bonds.

The term "support material" as used herein refers to chemically defined inorganic or organic materials with a porous structure and relatively high specific surface area. In one embodiment of the application, the support material is chosen based upon its adsorption activity and the type of separation required of the medium. Examples of support materials include, but are not limited to, activated charcoal, vermiculite, highly dispersive silicic acid (HDS), diatomaceous earth (Kieselguhr) and suitable polymers. A person skilled in the art would be able to readily select a suitable polymer for use as a support material in the methods of the present application.

The terms "ambient" or "ambient conditions" as used herein refer to the standard ambient temperature and pressure (SATP) established by the International Union of Pure and Applied Chemistry (IUPAC), wherein the temperature is about 25° C. and the absolute pressure is about 1 atm.

The term "precious metals" as used herein refers to rare, naturally occurring metallic chemical elements of high economic value. Examples of precious metals include, but are not limited to, technetium (Tc), Rhenium (Re) and Osmium (Os).

The term "exhaustion" as used herein refers to lowering the concentration of the precious metal below toxic or economically viable concentrations (i.e., lower than about 0.01 ppm).

The term "chelating agent" as used herein refers to molecules which can form several bonds to a single metal ion. In an embodiment, the chelating agent is a multidentate ligand.

The term "chemical warfare agent" as used herein refers to any toxic chemical or its precursor comprising an element-halogen bond. Examples of chemical warfare agents include, but are not limited to phosgene, diphosgene, nitrogen mustards, sulfur mustards, nerve agents and cyanogen chloride.

The term "decontamination" as used herein refers to the process of removing contaminants such as hazardous materials, including toxic chemicals from an object or substance.

II. Methods of the Application

The present application includes a method of reducing one or more halogenated compounds comprising contacting the one or more halogenated compounds with one or more compounds of Formula (I) under conditions for the reduction of the one or more halogenated compounds, wherein the compound of Formula (I) is:

$$R^1-\underset{H}{\underset{|}{\overset{R^2}{\overset{|}{N}}}}-\underset{R^4}{\underset{|}{\overset{R^3}{\overset{|}{C}}}}-\left[\underset{H}{\underset{|}{\overset{R^5}{\overset{|}{N}}}}-\underset{R^7}{\underset{|}{\overset{R^6}{\overset{|}{C}}}}\right]_n R^8 \qquad (I)$$

wherein $R^1$, $R^2$, $R^3$ and $R^8$ and each $R^5$ and $R^6$ are independently selected from $C_{1-6}$alkyl, $C_{3-10}$cycloalkyl, $C_{6-10}$aryl and $C_{5-10}$heteroaryl; or $R^2$ and $R^3$ and/or each $R^5$ and $R^6$, together with the nitrogen atoms to which they are attached, form a 5-7 membered carbocycle wherein 1 or 2 carbons are optionally replaced with $NR^9$;

$R^4$ and each $R^7$ are independently selected from H and $C_{1-6}$alkyl;

each $R^9$ is independently selected from $C_{1-6}$alkyl, $C_{3-10}$cycloalkyl, $C_{6-10}$aryl and $C_{5-10}$heteroaryl; and n is 0-18, and wherein the one or more halogenated compounds, is not $CA_4$, wherein A is halo.

The present application also includes a method of reducing one or more halogenated compounds comprising contacting the one or more halogenated compounds with one or more compounds of Formula (I) under conditions for the reduction of the one or more halogenated compounds, wherein the compound of Formula (I) is:

$$R^1-\underset{H}{\underset{|}{\overset{R^2}{\overset{|}{N}}}}-\underset{R^4}{\underset{|}{\overset{R^3}{\overset{|}{C}}}}-\left[\underset{H}{\underset{|}{\overset{R^5}{\overset{|}{N}}}}-\underset{R^7}{\underset{|}{\overset{R^6}{\overset{|}{C}}}}\right]_n R^8 \qquad (I)$$

wherein $R^1$, $R^2$, $R^3$ and $R^8$ and each $R^5$ and $R^6$ are independently selected from $C_{1-6}$alkyl, $C_{3-10}$cycloalkyl, $C_{6-10}$aryl and $C_{5-10}$heteroaryl; or $R^2$ and $R^3$ and/or each $R^5$ and $R^6$, together with the nitrogen atoms to which they are attached, form a 5-7 membered carbocycle wherein 1 or 2 carbons are optionally replaced with $NR^9$;

$R^4$ and each $R^7$ are independently selected from H and $C_{1-6}$alkyl;

each $R^9$ is independently selected from $C_{1-6}$alkyl, $C_{3-10}$cycloalkyl, $C_{6-10}$aryl and $C_{5-10}$heteroaryl; and n is 0-18, and wherein the one or more halogenated compounds, is not $CA_4$, wherein A is chloro.

In an embodiment, $R^1$, $R^2$, $R^3$ and $R^8$ and each $R^5$ and $R^6$ are independently selected from $C_{1-6}$alkyl, $C_{6-10}$aryl and $C_{5-10}$heteroaryl. In another embodiment, each $R^9$ is independently selected from $C_{1-6}$alkyl, $C_{6-10}$aryl and $C_{5-10}$heteroaryl. In an embodiment, n is 1-18. In another embodiment, n is 0.

In an embodiment, the compound of Formula (I) is a compound of Formula (I)(i):

$$R^1-\underset{H}{\underset{|}{N}}\overset{\frown{X}}{\underset{R^4}{\underset{|}{C}}}-\left[\underset{H}{\underset{|}{N}}\overset{\frown{X}}{\underset{R^7}{\underset{|}{C}}}\right]_n R^8 \qquad (I)(i)$$

wherein each X is independently $C_{2-4}$alkylene, wherein 1 or 2 of the $CH_2$ groups is optionally replaced with $NR^9$;

$R^1$ and $R^8$ and each $R^9$ are independently selected from $C_{1-6}$alkyl, $C_{3-10}$cycloalkyl, $C_{6-10}$aryl and $C_{5-10}$heteroaryl;

R⁴ and each R⁷ are independently selected from H and
$C_{1-6}$alkyl; and n is 0-18.

In an embodiment, each X is independently $C_{2-3}$alkylene, wherein 1 or 2 of the $CH_2$ groups is optionally replaced with $NR^9$. In another embodiment, each X is independently —$CH_2CH_2$—. In a further embodiment, $R^1$ and $R^8$ and each $R^9$ are independently selected from $C_{1-6}$alkyl, $C_{6-10}$aryl and $C_{5-10}$heteroaryl. In a further embodiment, $R^9$ is not present and $R^1$ and $R^8$ are independently selected from $C_{1-6}$alkyl and phenyl. It is an embodiment that $R^9$ is not present and $R^1$ and $R^8$ are $C_{1-6}$alkyl.

In an embodiment, n is 1-18. In another embodiment, n is 0.

In an embodiment, the compound of Formula (I)(i) is a compound of Formula (I)(i)(a), (I)(i)(b) or (I)(i)(c):

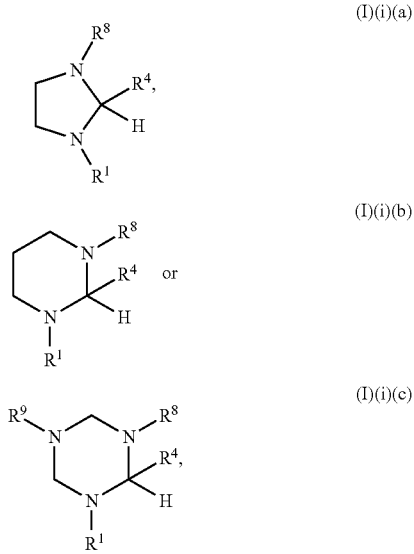

wherein $R^1$, $R^4$, $R^8$ and $R^9$ are as defined in the embodiments of the application.

In another embodiment, the compound of Formula (I)(i)(a) is:

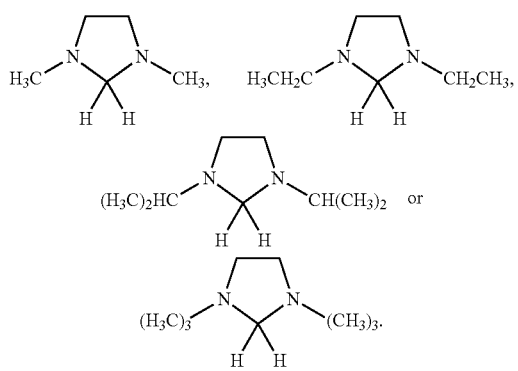

In a further embodiment, the compound of Formula (I)(i)(a) is:

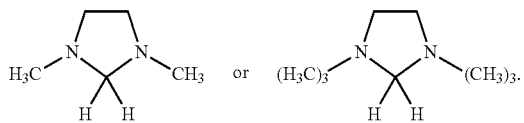

In an embodiment of the application, the compounds of Formula (I) are prepared from the reaction of primary and secondary amines with paraformaldehyde or aqueous formaldehyde using methods known in the art. For example, the cyclic compounds of Formula (I), in particular, the compounds of Formula (I)(i)(a) are prepared from ethylenediamine derivatives and the compounds of Formula (I)(i)(b) are prepared from 1,3-propylendiamine derivatives. Preparation of the compounds of Formula (I)(i)(c) are achieved by reacting polyamines, including but not limited to, diamines and triamines with aqueous formaldehyde or para-formaldehyde. In addition, preparation of the compounds of Formula (I)(i)(c) wherein compounds of Formula (I)(i)(c) are hexahydro-sym-triazines, are achieved by reacting primary amines with aqueous formaldehyde or paraformaldehyde. In an embodiment, the aminals are prepared neat or in solution. In another embodiment, the reactions are carried out on suitable support materials, including but not limited to, activated charcoal, vermiculite, Kieselguhr and/or polymers.

In an embodiment of the application, the compounds of Formula (I), wherein n is greater than 1, are prepared by reacting polyethylenimine (either linear or branched) with formaldehyde to obtain a polymer.

In an embodiment, the conditions for the reduction of the one or more halogenated compounds comprise treating the one or more halogenated compounds with an excess of one or more compounds of Formula (I), optionally, in an inert solvent at temperatures and for a time sufficient for the reduction of the one or more halogenated compounds. Examples of non-limiting reaction temperatures include, but are not limited to, about 10° C. to about 150° C., about 15° C. to about 120° C. or about 20° C. to about 100° C. Examples of non-limiting reaction times include, but are not limited to, about 1 minute to about 4 weeks, about 2 minutes to about a week, about 3 minutes to about 48 hours or about 5 minutes to about 24 hours. In an embodiment, the inert solvent is a hydrophobic inert solvent. Examples of non-limiting hydrophobic inert solvents include, but are not limited to, benzene, toluene, acetone, dioxane, hexanes, ethyl ether, ethyl acetate and $C_{1-6}$alkylOH (e.g. methanol, ethanol, 1-propanol, 2-propanol, 1-butanol, butan-2-ol or 2-methyl-1-propanol). In some embodiments, the halogenated hydrocarbon also serves as a solvent and is used in excess amounts.

In an embodiment, the conditions for the reduction of the one or more halogenated compounds comprise treating the one or more halogenated compounds with an excess of one or more compounds of Formula (I) and a transition metal catalyst at temperatures and for a time sufficient for the reduction of the one or more halogenated compounds. Examples of a transition metal catalyst include, but are not limited to, vanadium pentoxide ($V_2O_5$), iron pentacarbonyl ($Fe(CO)_5$), metallic platinum, palladium, cobalt and nickel. Examples of non-limiting reaction temperatures for the reduction of the one or more halogenated compounds using a transition metal catalyst include, but are not limited to, a temperature of about 10° C. to about 100° C., about 15° C. to about 80° C. or about 20° C. to about 60° C. Examples of non-limiting reaction times include, but are not limited to, about 1 minute to about 4 weeks, about 2 minutes to about a week, about 3 minutes to about 48 hours or about 5 minutes to about 24 hours. In an embodiment, the conditions for the reduction of the one or more halogenated compounds using a transition metal catalyst comprise dissolving and/or suspending the compound of Formula (I) and catalyst in an inert solvent such as a hydrophobic inert solvent. Examples of non-limiting hydrophobic inert solvents include, but are not limited to, benzene, toluene, acetone, dioxane, hexanes, ethyl ether, ethyl acetate and $C_{1-6}$alkylOH (e.g. methanol, ethanol, 1-propanol, 2-propanol, 1-butanol, butan-2-ol or 2-methyl-1-propanol). In an embodiment, the conditions for the reduction of the one or more halogenated compounds using a transition metal catalyst comprise neat reaction conditions, for example wherein the one or more halogenated compounds are in liquid form and are present in excess.

In an embodiment, the reduction of the one or more halogenated compounds result in the concomitant formation of halogen salts of the one or more compounds of Formula (I) as by-products. In an embodiment, the halogen salts precipitate from the reaction mixture. In another embodiment, the halogen salts are reduced to regenerate the one or more compounds of Formula (I).

In another embodiment, the salt of the compound of Formula (I) is:

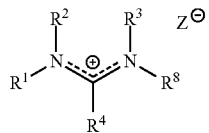

wherein $R^1$, $R^2$, $R^3$ and $R^8$ are independently selected from $C_{1-6}$alkyl, $C_{3-10}$cycloalkyl, $C_{6-10}$aryl and heteroaryl; or $R^2$ and $R^3$, together with the nitrogen atoms to which they are attached, form a 5-7 membered carbocycle wherein 1 or 2 carbons are optionally replaced with $NR^9$;

$R^4$ is selected from H and $C_{1-6}$alkyl;

$R^9$ is independently selected from $C_{1-6}$alkyl, $C_{3-10}$cycloalkyl, $C_{6-10}$aryl and heteroaryl; and Z is a halogen counteranion.

In an embodiment, the by-product salts of the compounds of Formula (I) are stable to air and water under ambient conditions.

In an embodiment, the compounds of Formula (I) are used in catalytic amounts in the presence of other reducing agents. In another embodiment, the other reducing agent is an inorganic reducing agent. In a further embodiment, the inorganic reducing agent is sodium dithionite. It is an embodiment that the catalytic amount of the compound of Formula (I) is generated in situ from the reduction of a halogen salt of the compound of Formula (I). In another embodiment, the halogen salt of the compound of Formula (I) is:

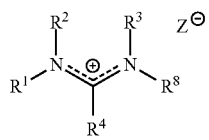

wherein $R^1$, $R^2$, $R^3$ and $R^8$ are independently selected from $C_{1-6}$alkyl, $C_{3-10}$cycloalkyl, $C_{6-10}$aryl and heteroaryl; or $R^2$ and $R^3$, together with the nitrogen atoms to which they are attached, form a 5-7 membered carbocycle wherein 1 or 2 carbons are optionally replaced with $NR^9$;

$R^4$ is selected from H and $C_{1-6}$alkyl; $R^9$ is independently selected from $C_{1-6}$alkyl, $C_{3-10}$cycloalkyl, $C_{6-10}$aryl and heteroaryl; and Z is a halogen counteranion.

In an embodiment, Z is Br.

In a further embodiment, the conditions for the reduction of the one or more halogenated compounds in the presence of other reducing agents comprise treating the one or more halogenated compounds with a catalytic amount of one or more compounds of Formula (I) or the halogen salt of one or more compounds of Formula (I) as defined in the embodiments of the application in the presence of sodium dithionite and a suitable base, for example, sodium bicarbonate, optionally, in an inert solvent at temperatures and for a time sufficient for the reduction of the one or more halogenated compounds. Examples of non-limiting reaction temperatures include, but are not limited to, about 10° C. to about 150° C., about 15° C. to about 100° C. or about 20° C. to about 40° C. Examples of non-limiting reaction times include, but are not limited to, about 1 minute to about 4 weeks, about 2 minutes to about a week, about 3 minutes to about 48 hours or about 30 minutes to about 24 hours. Examples of non-limiting inert solvents include, but are not limited to, benzene, toluene, acetone, dioxane, hexanes, ethyl ether, ethyl acetate, $C_{1-6}$alkylOH (e.g. methanol, ethanol, 1-propanol, 2-propanol, 1-butanol, butan-2-ol or 2-methyl-1-propanol) and water. In an embodiment, the inert solvent is a mixture of benzene and water.

In an embodiment, the compounds of Formula (I) have one or more stereogenic centers for enantioselective reductions.

In an embodiment, the one or more halogenated compounds are selected from halogenated arenes and linear and/or cyclic halogenated alkanes. In another embodiment, the linear and/or cyclic halogenated alkanes are selected from 2-bromo-2-chloro-1,1,1-trifluoroethane, 1,2-dibromoethane, 1,2-dichloroethane, $CH_3Br$, $CH_2Br_2$, $CHBr_3$, $CHCl_3$, $C_2H_2I_2$, 1,2-dibromocyclohexane and 1-bromoadamantane. In another embodiment, the linear halogenated alkanes are selected from $CH_3Br$, $CH_2Br_2$, $CHBr_3$, $CHCl_3$ and $C_2H_2I_2$. In a further embodiment, the cyclic halogenated alkane is 1-bromoadamantane. It is an embodiment that the halogenated arene is 4,4'-dichlorodiphenyltrichloroethane (DDT). In yet a further embodiment, the halogenated arene is selected from 1,3,5-tribromobenzene, 1,3-dibromobenzene, bromobenzene, 1,4-diiodobenzene and iodobenzene.

In an embodiment, the one or more halogenated compounds are linear cyclic halogenated alkanes comprising a C—Br bond and one or more C—Cl and/or C—F bonds and the method comprises the selective reduction of the C—Br bond. In another embodiment, the linear cyclic halogenated alkane is 2-bromo-2-chloro-1,1,1-trifluoroethane.

In an embodiment, the one or more halogenated compounds are selected from 1,2-dichloroalkanes, 1,2-dibromoalkanes and 1,2-dibromocycloalkanes. In another embodiment of the present application, the one or more halogenated compounds are selected from a 1,2-dichloro$C_{1-10}$alkane, a 1,2-dibromo$C_{1-10}$alkane and a 1,2-dibromo$C_{4-10}$cycloalkane. In a further embodiment, the one or more halogenated compounds are selected from a 1,2-dichloro$C_{1-6}$alkane and a 1,2-dibromo$C_{1-6}$alkane. It is an embodiment that the one or more halogenated compounds are a 1,2-dibromocycloC$_{5-7}$cycloalkane. In another embodiment, the one or more halogenated compounds are selected from 1,2-dibromoethane, 1,2-dichloroethane and 1,2-dibromocyclohexane.

In an embodiment, the one or more halogenated compounds are comprised in soil and the reduction of the one or more halogenated compounds decontaminates the soil of halogenated compounds. In another embodiment, the one or more halogenated compounds are comprised in a chemical warfare agent and the reduction of the one or more halogenated compounds degrades or detoxifies the chemical warfare agent.

The present application also includes a method of recovering precious metals, the method comprising:
a) adsorbing one or more compounds of Formula (I) as defined in the embodiments of the application onto a support material;
b) contacting a solution comprising precious metals with the adsorbed one or more compounds of Formula (I) under conditions for the reduction of the precious metals; and
c) removing the adsorbed precious metals from the support material.

In an embodiment, the support material is selected from highly dispersive silicic acid (HDS), activated charcoal, diatomaceous earth (kieselguhr) and vermiculite. In another embodiment, the support material is selected from HDS, activated charcoal and kieselguhr. In a further embodiment, the support material is selected from HDS and activated charcoal.

In an embodiment, the precious metals are selected from palladium (Pd), platinum (Pt), rhodium (Rh), iridium (Ir), gold (Au), silver (Ag) technetium (Tc), rhenium (Re) and osmium (Os).

In an embodiment, the adsorption of one or more compounds of Formula (I) onto the support material results in a colorless material. In another embodiment, the colorless material is washed with an aqueous solvent. In a further embodiment, the solvent is water.

In an embodiment, the reduction of the precious metals is carried out at temperatures and under pressure conditions for the conversion to proceed to a sufficient extent. Examples of non-limiting temperatures include, but are not limited to, −30° C. to about 100° C. or about −20° C. to about 80° C. Examples of non-limiting pressure conditions include, but are not limited to, about 1 atm or slightly elevated pressures such as up to about 2 atm. In an embodiment, the reduction of the precious metals is carried out under ambient conditions.

In an embodiment, contact of the solution of precious metals with the one or more compounds of Formula (I) leads to discoloration of the stationary phase indicating the recovery and exhaustion of the precious metals. In another embodiment, the discoloration is black.

In an embodiment, the adsorbed precious metals are removed using chemical reagents. In another embodiment, the chemical reagents are selected from oxidants, cyanides, phosphines, chelating agents and thiosulfates. In another embodiment, the chemical reagent is an oxidant. In a further embodiment, the oxidant is selected from a stream of oxygen and air. In yet a further embodiment, the precious metals are recovered as volatile oxides.

The present application also includes a method of reducing a chlorate or perchlorate comprising contacting the chlorate or perchlorate (e.g. in aqueous solution) with one or more compounds of Formula (I) as defined in the embodiments of the application under conditions for the reduction of the chlorate or perchlorate.

EXAMPLES

The following non-limiting examples are illustrative of the present application:

Example 1: Reduction of Halocarbons

Starting Materials: 1,3-di-tert-butyl-imidazolidine 1ll (R=tBu) and 1,3-di-methyl-imidazolidine 1H (R=Me) were obtained from the respective N,N'-di-alkyl-1,2-diaminoethanes as described elsewhere [7,8]. All other chemicals were obtained from Sigma-Aldrich Inc. and used as received.

A. General Procedure and Analytical Data

The reductions were carried out with a slight excess of 1H (1.1 equivalent per reducible halogen). In nonpolar solvents like hexanes or diethyl ether, onset of the reduction was indicated by the appearance of a turbidity and subsequent precipitation of the salts 1$^+$X$^-$. Control experiments under inert gas with degassed materials did not show noticeably different reaction rates or products. For the less reactive aryl halides and chloromethanes, heating was used to drive the reaction to completion. The progress of the reductions was monitored by $^1$H-NMR. After completion of the reaction, the salts [1]X were isolated by filtration, washed with diethyl ether and dried in vacuo. Yield 85-95%. Traces of [4]X can be removed from [1]X by recrystallization from 95% ethanol.

1,3,5-Tribromobenzene

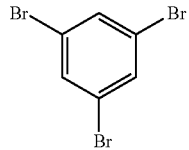

$^1$H-NMR (400 MHz, CDCl$_3$): δ 7.61 ppm. $^{13}$C-NMR (CDCl$_3$): δ 133.0 [C-2,4,6] 123.4 [C-1,3,5].

1,3-Dibromobenzene

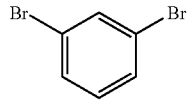

$^1$H-NMR (400 MHz, CDCl$_3$): δ 7.67, 7.43, 7.11. $^{13}$C-NMR (CDCl$_3$): δ 134.2 [C-2], 131.2 [C-5], 130.3 [C-4,6], 123.1 [C-1,3].

1,3-Di-tert-butyl-imidazolidine (1H)

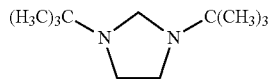

Colorless oil, $^1$H-NMR (C$_6$D$_6$): δ 3.67 [s, NCH$_2$N], 2.75 [s, CH$_2$CH$_2$], 1.09 [s, (CH$_3$)$_3$C]. $^{13}$C-NMR (C$_6$D$_6$): δ 63.3 [NCH$_2$N], 52.0. [C(CH$_3$)$_3$], 46.0 [CH$_2$CH$_2$], 26.1 [C(CH$_3$)$_3$]. EI-MS 184 (15)[M$^+$], 183 (97), 127 (30), 113 (100), 98 (8), 84 (30), 71 (89), 57 (28).

1,3-Di-tert-butyl-imidazolidinium chloride [1]Cl

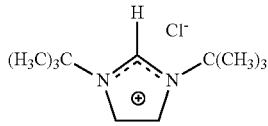

Colorless crystals, m.p. (from chloroform) 201-203° C. $^1$H-NMR (CDCl$_3$): δ 1.55 p.p.m. [s, C(CH$_3$)$_3$], 4.05 [s, NCH$_2$], 8.85 [s, N$_2$CH$^+$]. $^{13}$C-NMR (400 MHz, CDCl$_3$): δ 28.2 [C(CH$_3$)$_3$], 45.3 [NCH$_2$], 57.2 [C(CH$_2$)$_2$], 154.1.

1,3-Di-tert-butyl-imidazolidinium bromide [1]Br

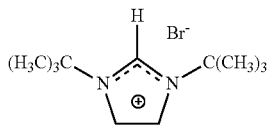

Colorless crystals, m.p. (from chloroform) 230-231° C. (dec.). $^1$H-NMR (CDCl$_3$): δ 1.56 p.p.m. [s, C(CH$_3$)$_3$], 4.10 [s, NCH$_2$], 8.46 [s, N$_2$CH$^+$]. $^{13}$C-NMR (CDCl$_3$): δ 28.3 p.p.m. [C(CH$_3$)$_3$], 45.5 [NCH$_2$], 57.2 [C(CH$_2$)$_2$], 153.1 [CH$^+$]. Electrospray MS(+) 183(100), 173(10), 117(5), 100 (9), 57(5), 41(6). ES-MS(−): 79/81.

1,3-Di-tert-butyl-imidazolium chloride [4]Cl

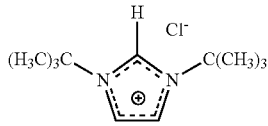

m.p. 209-210° C. $^1$H-NMR (400 MHz, CDCl$_3$): δ 1.80 ppm. [s, C(CH$_3$)$_3$], 7.54 [s, HC=CH], 10.54 [s, CH$^+$]. $^{13}$C-NMR (400 MHz, CDCl$_3$): δ 30.3 ppm. [s, C(CH$_3$)$_3$], 60.8 [C(CH$_3$)$_3$] 119.7 [HC=CH] 134.5 [d, N$_2$CH$^+$].

1,3-Di-tert-butyl-imidazolium bromide [4]Br

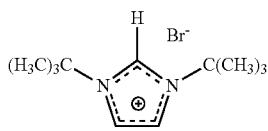

m.p. 219-220° C. $^1$H-NMR (400 MHz, CDCl$_3$): δ 1.85 ppm. [s, C(CH$_3$)$_3$], 7.39 [s, HC=CH], 10.37 [s, CH$^+$]. $^{13}$C-NMR (400 MHz, CDCl$_3$): δ 30.4 ppm. [C(CH$_3$)$_3$], 61.2 [C(CH$_3$)$_3$], 118.9 [HC=CH], −135.2.

1,3-Dimethyl-imidazolidine

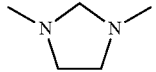

Colorless oil. $^1$H NMR (C$_6$D$_6$): d 2.20 [s, 6H, NCH$_3$], 2.56 [s, 4H, CH$_2$CH$_2$], 3.18 [s, 2H, NCH$_2$N]. $^1$H NMR (CDCl$_3$): δ 2.36 [s, 6H, NCH$_3$], 2.76 [s, 4H, CH$_2$CH$_2$], 3.28 [s, 2H, NCH$_2$N]. $^{13}$C NMR (CDCl$_3$): 41.6 [NCH$_3$], 54.7 [CH$_2$CH$_2$], 79.0 [NCH$_2$N]. $^{15}$N NMR (CDCl$_3$) −339.9. EI-MS (70 eV, m/z, rel. int. %): m/z=100 (4) [M]+., 99 (41), 85 (24), 57 (21), 42 (100), 28 (32), 18 (35). FT-IR (neat, NaCl) 1455 s, 1370 s, 1228 s, 1115 s, 1033 m, 967 w, 921 m, 872 s, 810 s.

1,3-Dimethyl-imidazolidinium bromide

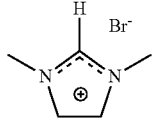

m.p. 189-191° C. (from chloroform). $^1$H-NMR (CDCl$_3$): δ 3.35 ppm. [s, NCH$_3$], 4.01 [s, 4H, NCH$_2$], 9.54 [s, 1H, N$_2$CH$^+$]. $^{13}$C-NMR (CDCl$_3$): δ 35.2 [N—CH$_3$], 50.9 [NCH$_2$], 159.4 [N$_2$CH]. $^1$H NMR (DMSO-D$_6$): 3.08 [s, 18H, N—CH$_3$], 3.85 [s, 4H, NCH$_2$], 8.41 [s, 1H, N$_2$CH$^+$]. $^{13}$C NMR (DMSO-D$_6$): 34.1 [N—CH$_3$], 50.2 [NCH$_2$], 158.3 [NCH$^+$].

1,3-Diphenyl-imidazolidine

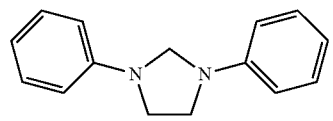 [SMILES: c1ccc(N2CCN(c3ccccc3)C2)cc1]

Colorless plates, m. p. 127° C. $^1$H NMR (CDCl$_3$): δ 3.66 [s, 4H, CH$_2$CH$_2$], 4.67 [s, 2H, N$_2$CH$_2$], 6.68 [d, 4H, $^3$J=8.1 Hz, ortho-CH], 6.80 [t, 2H, $^3$J=7.3 Hz, para-CH], 7.30 [t, 4H, $^3$J=7.7 Hz, meta-CH]. $^{13}$C NMR (C$_6$D$_6$): δ 46.5 [CH$_2$CH$_2$], 65.9 [N$_2$CH$_2$], 112.4 [ortho-CH], 117.6 [para-CH], 129.4 [meta-CH], 146.4 [ipso-C]. EI-MS (70 eV, rel. int. %): m/z=224 (60) [M]$^+$., 223 (81), 119 (70), 106 (63), 91 (100), 77 (54), 65 (9), 51 (21). IR (Nujol, NaCl, cm$^{-1}$): 1601 m, 1574 m, 1502 s, 1327 m, 1239 m, 1186 m, 1158 m, 995 m, 868 w, 745 s, 693 s.

1,3-Diphenyl-imidazolidinum bromide

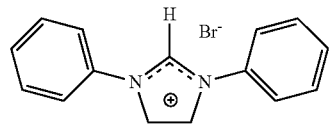

$^1$H NMR (CDCl$_3$): δ 4.63 [s, 4H, CH$_2$CH$_2$], 7.21 [m, 2H, p-phenyl] 7.37 [m, 4H, phenyl] 7.82 [d, 8.3 Hz, 4H, phenyl], 10.80 [s, 1H, N$_2$CH$^+$], $^{13}$C NMR (CDCl$_3$): δ 48.6 [CH$_2$CH$_2$], 118.9 [meta-phenyl], 127.8 [p-phenyl], 130.0 [ortho], 135.0 [ipso], 150.9 [N$_2$CH$^+$]. Electrospray MS(+) 303(10) [M+HBr], 223(100) [M], 197(10), 102(9). ES-MS (−): 79/81. IR (Nujol) 1619 s, 1588 s, 1494 w, 1462 s, 1377 m, 1344 w, 1296 s, 761 m, 688 m.

B. Results and Discussion

A systematic examination of halogenated methanes revealed that with the notable exception of CH$_3$Cl and CH$_2$Cl$_2$, all chloromethanes and bromomethanes were reduced at room temperature. The reactivity increased from CH$_3$Br<CHCl$_3$<CH$_2$Br$_2$<CHBr$_3$. The nature of the employed solvent (ethanol, hexanes, excess of 1H or excess of the halogenated hydrocarbon) does not seem to significantly influence the reaction rates. After completion of the reduction, the salts [1]X were obtained in nearly quantitative yield.

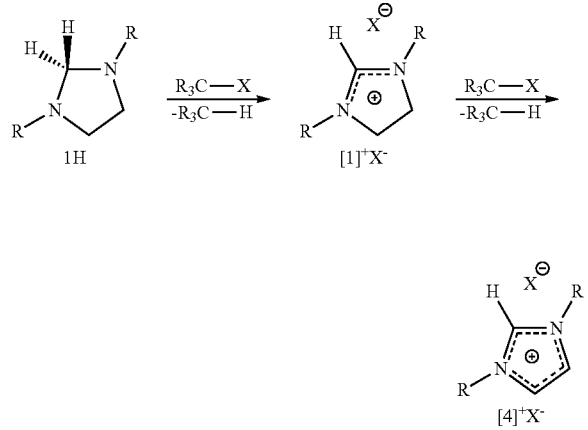

Scheme 1.

Reduction of carbon halogen bonds C—X by imidazolidines 1H (R=Me, tBu).

In the presence of an excess of imidazolidine 111, multiple, subsequent reductions were feasible for CHBr$_3$, CH$_2$Br$_2$ and C$_6$H$_6$Br$_3$. An excess of the halogenated hydrocarbon and prolonged reaction times can lead to further oxidation of [1]X to the imidazolium salts [4]X, but this second dehydrogenation step was too slow to compete with the oxidation of 1H.

Surprisingly, bromobenzene was also reduced at room temperature but required heating (100° C., 24 h) for a complete reduction.

To test for the ability of 1H to reduce polybrominated benzene derivatives used as flame retardants [22], 1,3,5 tribromobenzene was investigated. Reduction to 1,3-dibromobenzene was achieved within minutes. While bromobenzene was not detected, the formation of benzene suggests, while not wishing to be limited by theory, that it had been present as intermediate of the total reduction.

Chlorobenzene was found to be inert at room temperature but was slowly reduced at elevated temperatures (200° C.).

The unexpected reactivity of the model 1H suggests that halogenated hydrocarbons may be able to disrupt biochemical pathways involving MTHF.

Example 2: Reduction of an aryl C—Br bond

Reaction of 1,3,5-tribromobenzene with 1,3-di-tert-butyl-imidazolidine to provide 1, 3-dibromobenzene

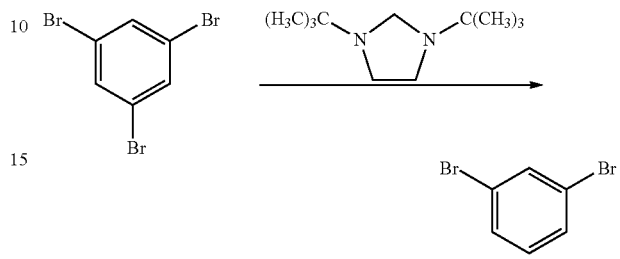

In a 100 mL Schlenk flask, 1,3-di-tert-butyl-imidazolidine (0.31 g, 1.70 mmol) was dissolved in 3 mL of 1,4-dioxane. A solution of 1,3,5-tribromobenzene (0.18 g, 0.56 mmol) in 3 mL of 1,4-dioxane was added and the vessel was heated at 120° C. for 4 hours. $^1$H-NMR, $^{13}$C-NMR, and GC-MS of the supernatant showed conversion of 1,3,5-tribromobenzene to 1,3-dibromobenzene. $^1$H-NMR (400 MHz, CDCl$_3$): δ 7.13 t, 7.44 dod, 7.68 t. $^{13}$C-NMR (400 MHz, CDCl$_3$): δ 122.9 [C-1,3], 130.1 [C-4,6], 131.1 [C-5], 134.1 [C-2]. EI-MS (pos. ions, 70 eV) m/z (rel. int.)=236 (100) [M]+', 155 (72), 118 (5), 75 (41), 61 (3). The white precipitate that was formed was the imidazolidinium bromide salt. Yield 0.28 g, 65%. Prolonged heating led to complete reduction (formation of benzene).

Example 3: Reduction of an Alkyl C—I Bond

Reaction of 1, 2-diiodoethane with 1, 3-di-tert-butyl-imidazolidine to provide ethylene

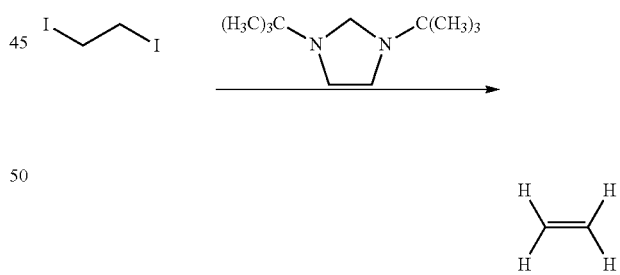

A solution of 1,2-diiodoethane (0.09 g, 0.32 mmol) in 2 mL of benzene-d$_6$ was added to an NMR tube and frozen with liquid nitrogen. 1,3-di-tert-butyl-imidazolidine (0.05 g, 0.27 mmol) was added dropwise and the NMR tube was flame sealed under vacuum. 3 minutes after warming to room temperature the liquid in the tube turned light yellow and a brown precipitate fell to the bottom. After 30 minutes the production of solid ceased. $^1$H-NMR and $^{13}$C-NMR of the reaction mixture showed complete consumption of 1,3-di-tert-butyl-imidazolidine and production of ethylene. $^1$H-NMR (400 MHz, C$_6$D$_6$): δ 5.25, s. $^{13}$C-NMR (400 MHz, C$_6$D$_6$): δ 122.9.

Example 4: Reduction of an Aryl C—I Bond

Reaction of 1, 4-diiodobenzene with
1,3-di-tert-butyl-imidazolidine to provide
iodobenzene

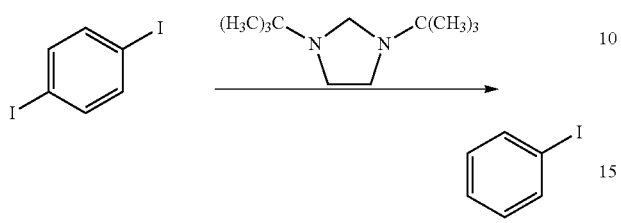

In a 100 mL Schlenk flask, 1,3-di-tert-butyl-imidazolidine (0.16 g, 0.87 mmol) was dissolved in 5 mL of 1,4-dioxane. A solution of 1,4-diiodobenzene (0.15 g, 0.45 mmol) in 3 mL of 1,4-dioxane was added with stirring. After 30 minutes of heating at 100° C. a fine white solid formed. The precipitate continued to collect after heating for 1 day. The final off-white product was washed with ether. Yield 0.07 g, 26%. $^1$H-NMR and $^{13}$C-NMR of the precipitate showed formation of the imidazolidinium iodide salt. $^1$H-NMR (400 MHz, CDCl$_3$): δ 1.56 [s, 18H, C(CH$_3$)$_3$], 4.09 [s, 4H, NCH$_2$], 8.13 [s, 1H, N$_2$CH$^+$]. $^{13}$C-NMR (400 MHz, CDCl$_3$): δ 28.2 [C(CH$_3$)$_3$], 45.5 [NCH$_2$], 57.2 [C(CH$_2$)$_2$], 152.2 [CH$^+$]. GC-MS of the supernatant showed conversion of 1,4-diiodobenzene to iodobenzene. EI-MS (pos. ions, 70 eV) m/z (rel. int.)=204 (100) [M]$^+$, 127 (7.8), 77 (69), 51 (22).

Example 5: Reduction of a Tertiary Halide Bond

Reaction of 1-bromoadamantane with
1,3-di-tert-butyl-imidazolidine to provide
adamantane

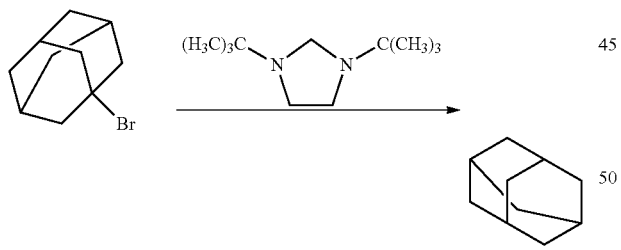

In a 25 mL stainless steel autoclave, 1,3-di-tert-butyl-imidazolidine (0.45 g, 2.4 mmol) was dissolved in 4 mL of diethyl ether. A solution of 1-bromoadamantane (0.51 g, 2.37 mmol) in 4 mL of diethyl ether was added and the vessel was heated at 150° C. for 1 week. After heating, there was white precipitate floating in a light yellow liquid. $^1$H-NMR and $^{13}$C-NMR of the precipitate showed formation of the imidazolidinium bromide salt. Yield 0.14 g, 45%. $^{13}$C-NMR and GC-MS of the yellow supernatant showed conversion of 1-bromoadamantane to adamantane. $^{13}$C-NMR (400 MHz, CDCl$_3$): δ 28.3 [3° carbon], 37.7 [2° carbon]. EI-MS (pos. ions, 70 eV), m/z (rel. int.)=136 (100) [M]$^+$, 121 (11), 107 (10), 93 (42), 79 (38), 67 (15), 53 (7).

Example 6: Selective Reduction of Aqueous Silver in the Presence of Aqueous Lead and zinc with 1,3-di-tert-butyl-imidazolidine In a 100 mL Schlenk tube, 1,3-di-tert-butyl-imidazolidine (0.56 g, 3.0 mmol) was added dropwise to 5 mL of a 10% aqueous solution of silver, lead, and zinc nitrates. White precipitate immediately formed and after 1 minute a shiny mirror of metallic silver was deposited on the sides of the tube.

Example 7: Reduction of Aqueous Gold

Reaction of auric acid with
1,3-di-tert-butyl-imidazolidine

In a 100 mL Schlenk tube, 1,3-di-tert-butyl-imidazolidine (0.28 g, 1.5 mmol) was added to a 10% aqueous solution of auric acid. After 3 minutes a mirror of metallic gold formed on the sides of the tube.

Example 8: Reduction of Aqueous Chlorate to Chloride

Reaction of potassium chlorate with 1,
3-di-tert-butyl-imidazolidine

In a 6 dram vial, potassium chlorate (0.12 g, 0.98 mmol) was dissolved in 2 mL of deuterium oxide. 1,3-di-tert-butyl-imidazolidine (0.25 g, 1.35 mmol) was added with stirring. After 4 hours of heating at 100° C., a fine white solid formed. The precipitate continued to collect after heating for 1 day. The final white product was washed with diethyl ether. Yield 0.17 g, 47%. $^1$H-NMR and $^{13}$C-NMR of the precipitate showed formation of the imidazolidinium chloride salt. $^1$H-NMR (600 MHz, D$_2$O): δ 1.35 [s, 18H, C(CH$_3$)$_3$], 3.96 [s, 4H, NCH$_2$], 8.42 [s, 1H, N$_2$CH$^+$]. $^{13}$C-NMR (600 MHz, CDCl$_3$): δ 26.9 [C(CH$_3$)$_3$], 44.9 [NCH$_2$], 56.1 [C(CH$_2$)$_2$], 171.1 [CH$^+$]. GC-MS of the supernatant showed conversion of 1,3-di-tert-butyl-imidazolidine to 1,3-di-tert-butyl-imidazolidine-2-one. EI-MS (pos. ions, 70 eV) m/z (rel. int.)=198 (9) [M]$^+$, 183 (55), 142 (3), 127 (100), 86 (10), 70 (8), 57 (19).

Example 9: Reduction of Aqueous Perchlorate to Chloride

Reaction of ammonium perchlorate with
1,3-di-tert-butyl-imidazolidine

In a 6 dram vial, ammonium perchlorate (0.06 g, 0.51 mmol) was dissolved in 1 mL of deuterium oxide. 1,3-di-tert-butyl-imidazolidine (0.13 g, 0.71 mmol) was added with stirring. After 3 hours of heating at 100° C. a fine white solid formed. The precipitate continued to collect after heating for 1 day. The final white product was washed with ether. Yield 0.17 g, 47%. $^1$H-NMR and $^{13}$C-NMR of the precipitate showed formation of the imidazolidinium chloride salt. $^1$H-NMR (600 MHz, D$_2$O): δ 1.35 [s, 18H, C(CH$_3$)$_3$], 3.96 [s, 4H, NCH$_2$], 8.42 [s, 1H, N$_2$CH$^+$]. $^{13}$C-NMR (600 MHz, CDCl$_3$): δ 26.9 [C(CH$_3$)$_3$], 44.9 [NCH$_2$], 56.1 [C(CH$_2$)$_2$], 171.1 [CH$^+$]. GC-MS of the supernatant showed conversion of 1,3-di-tert-butyl-imidazolidine to 1,3-di-tert-butyl-imidazolidine-2-one. EI-MS (pos. ions, 70 eV) m/z (rel. int.)=198 (9) [M]$^+$, 183 (55), 142 (3), 127 (100), 86 (10), 70 (8), 57 (19).

Example 10: Selective Reduction of an Alkyl C—Br Bond in the Presence of C—Cl and C—F Bonds Reaction of 2-bromo-2-chloro-1,1,1-trifluoroethane with 1, 3-di-tert-butyl-imidazolidine to provide 2-chloro-1,1,1-trifluoroethane

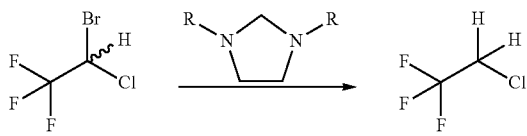

Halothane (2-bromo-2-chloro-1,1,1-trifluoroethane, 80 g, 0.41 mol) and imidazolidine (1.1 eqiv., R=Me, tBu, or Ph) were added to an autoclave and stirred at room temperature for 24 h. NMR spectroscopy ($^1$H, $^{13}$C, and $^{19}$F) of the reaction mixture showed complete consumption of the starting material Halothane® (2-bromo-2-chloro-1,1,1-trifluoroethane). The product was clean 2-chloro-1,1,1-trifluoroethane, which was vented from the autoclave and collected in a liquid nitrogen trap.

$^1$H-NMR (600 MHz, C$_6$D$_6$): δ 2.78 [q, $^3$J($^1$H, $^{19}$F)=8.5 Hz]. $^{13}$C-NMR (600 MHz, C$_6$D$_6$): δ 40.1 [q, $^2$J($^{13}$C, $^{19}$F)=37.7 Hz, CH$_2$], 123.1 [q, $^1$J($^{13}$C, $^{19}$F)=275.7 Hz, CF$_3$]. $^{19}$F-NMR (600 MHz, C$_6$D$_6$ vs. CFCl$_3$): δ 71.6 [t, $^3$J($^1$H, $^{19}$F)=8.5 Hz].

Example 11: Reduction of 1,2-Dibromoalkanes to Prepare Vinyl Bromides

Reaction of 1, 2-dibromoethane with 1, 3-di-tert-butyl-imidazolidine to provide vinyl bromide

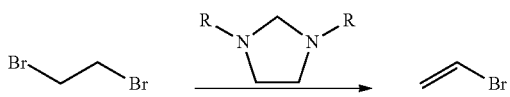

1,2-dibromoethane (75 g, 0.40 mol) and imidazolidine (2.2 eqiv., R=Me, tBu, or Ph) were added to an autoclave and stirred at room temperature for 24 h. NMR spectroscopy ($^1$H and $^{13}$C) of the reaction mixture showed complete consumption of the starting material. The product was clean vinyl bromide, which was vented from the autoclave and collected in a liquid nitrogen trap.

$^1$H-NMR (400 MHz, C$_6$D$_6$): δ 5.42 [dod, $^2$J=1.86 Hz, $^3$J=7.12 Hz]. δ 5.51 [dod, $^2$J=1.86 Hz, $^3$J=14.9 Hz]. δ 6.01 [dod, $^2$J=7.12 Hz, $^3$J=14.9 Hz]. $^{13}$C-NMR (400 MHz, C$_6$D$_6$): δ 114.0, 121.7.

Example 12: Reduction of 1,2-Dichloro Compounds to Prepare Vinyl Chlorides

Reaction of 1, 2-dichloroethane with 1, 3-di-tert-butyl-imidazolidine to provide vinyl chloride

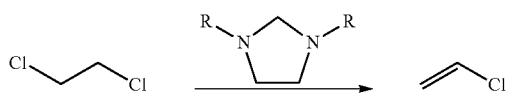

1,2-dichloroethane (80 g, 0.81 mol) and imidazolidine (2.2 eqiv., R=Me, tBu, or Ph) were added to an autoclave and stirred at 150° C. for 72 h. NMR spectroscopy ($^1$H and $^{13}$C) of the reaction mixture showed complete consumption of the starting material. The product was clean vinyl chloride, which was vented from the autoclave and collected in a liquid nitrogen trap.

$^1$H-NMR (400 MHz, C$_6$D$_6$): δ 4.84 [dod, $^2$J=−1.6 Hz, $^3$J=7.2 Hz]. δ 5.26 [dod, $^2$J=−1.6 Hz, $^3$J=14.7 Hz]. δ 5.80 [dod, $^2$J=7.2 Hz, $^3$J=14.7 Hz].

Example 13: Reduction of 1,2-Dibromocycloalkanes to Prepare Cycloalkenes

Reaction of 1, 2-dibromocyclohexane with 1, 3-di-tert-butyl-imidazolidine to provide cyclohexene

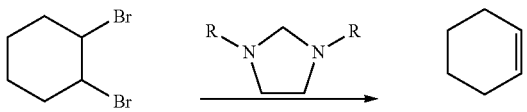

1,2-dibromocyclohexane (45 g, 0.19 mol) and imidazolidine (2.2 eqiv., R=Me, tBu, or Ph) were added to a Schlenk tube and stirred at room temperature for 24 h. NMR spectroscopy ($^1$H and $^{13}$C) of the reaction mixture showed complete consumption of the starting material. The product was clean cyclohexene.

$^1$H-NMR (400 MHz, CDCl$_3$): δ 1.61 [m], 1.99 [m], 5.67 [t]. $^{13}$C-NMR (400 MHz, CDCl$_3$): δ 22.6, 25.1, 127.2.

Example 14: Dehalogenation of Chlorinated Pesticides

Reaction of 4,4'-dichlorodiphenyltrichloroethane (DDT) with 1,3-di-tert-butyl-imidazolidine to provide 1,1-dichloro-2,2-bis(4-chlorophenyl)ethane (DDD), 1,1-dichloro-2, 2-bis(4-chlorophenyl)ethene (DDE), 1-chloro-2,2-bis(4-chlorophenyl)ethene (DDMU), 4,4'-dichlorobenzophenone (DBP), and 1,1-bis(4-chlorophenyl)methane (DDM)

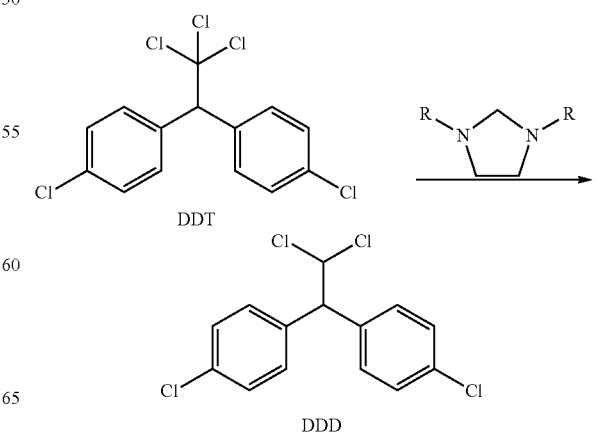

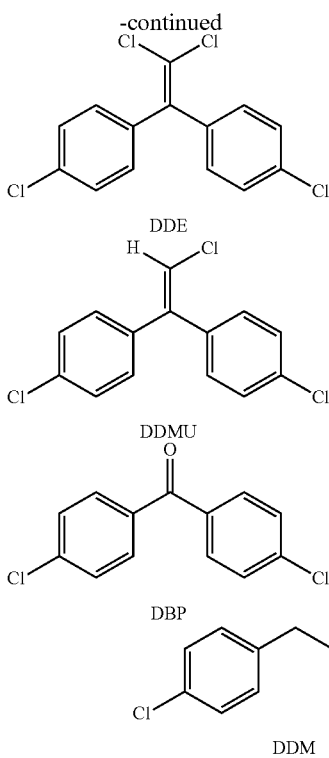

DDT (2.8 g, 7.8 mmol), benzene (20 mL), and imidazolidine (5.5 eqiv., R=Me, tBu, or Ph) were added to a 50 mL round bottom flask and stirred magnetically at room temperature. After 12 hours, GC-MS showed the complete conversion of DDT to DDD, DDE, DDMU, DBP, and DDM. After 24 hours, GC-MS showed complete conversion to DDMU, DBP, and DDM. Retention times for all products were compared to those of the blank analytical standards. DDD: GC-MS: $t_r$=15.77 min, m/z (rel. in %): 319(1)[M$^+$], 235(100), 165(55), 88(5). DDE: GC-MS: $t_r$=14.95 min, m/z (rel. in %): 317(85)[M$^+$], 246(100), 210(15), 176(33), 105 (12), 87(9). DDMU: GC-MS: $t_r$=14.36 min, m/z (rel. in %): 282(80)[M$^+$], 247(21), 212(100), 176(44), 123(11), 105(10), 88(18), 75(16). DBP: GC-MS: $t_r$=13.61 min, m/z (rel. in %): 250(34)[M$^+$], 215(12), 139(100), 111(38), 75(28). DDM: GC-MS: $t_r$=12.81 min, m/z (rel. in %): 236(49)[M$^+$], 201 (100), 165(78), 125(13), 89(15), 82(11).

Example 15: Catalytic Reduction of Halocarbon with Imidazolidines and an Inorganic Reducing Agent Reaction of Carbon Tetrabromide with Catalytic Imidazolidines (7.5 Mol %) in the Presence of Sodium Dithionite

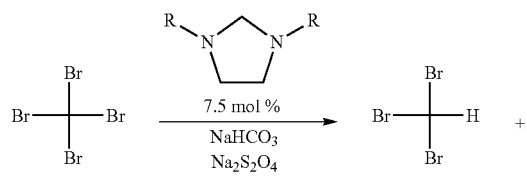

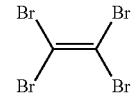

Carbon tetrabromide (7.15 g, 21.6 mmol), benzene (120 mL), sodium bicarbonate (8.2 g, 97.6 mmol), sodium dithionite (4.4 g, 25.3 mmol), water (250 mL), and a catalytic amount of imidazolidine (7.5 mol %, R=Me, tBu, or Ph) were added to a 500 mL round bottom flask and stirred magnetically at room temperature. After 14 hours GC-MS and NMR of the organic layer showed the complete conversion of carbon tetrabromide to bromoform and 1,1,2,2-tetrabromoethylene. CHBr$_3$: $^1$H-NMR (600 MHz, CDCl$_3$): δ 6.71 [s]. $^{13}$C-NMR (600 MHz, CDCl$_3$): δ 9.73. GC-MS: $t_r$=5.73 min, % area=61%, m/z (rel. int %): 251(14)[M$^+$], 173(100), 91(17), 80(15). C$_2$Br$_4$: $^{13}$C-NMR (600 MHz, CDCl$_3$): δ 92.3. GC-MS: $t_r$=8.75 min, % area=31%, m/z (rel. in %): 344(100)[M$^+$], 263(72), 184(55), 103(19), 91(8), 79(17).

Example 16: In Situ Formation of Imidazolidines from Imidazolidinium Salts; Catalytic Reduction of Halocarbon with Imidazolidinium Bromides and an Inorganic Reducing Agent Reaction of Carbon Tetrabromide with Catalytic Amounts of Imidazolidinium Bromides (7.5 Mol %) in the Presence of Sodium Dithionite Carbon tetrabromide (7.20 g, 21.7 mmol), benzene (130 mL) sodium bicarbonate (8.19 g, 97.5 mmol) sodium dithionite (4.4 g, 25.3 mmol), water (250 mL), and a catalytic amount of imidazolidinium bromide (7.5 mol %, R=Me, tBu, or Ph) were added to a 500 mL round bottom flask and stirred magnetically at room temperature. After 36 hours GC-MS and NMR of the organic layer showed the complete conversion of carbon tetrabromide to bromoform and 1,1,2,2-tetrabromoethylene. CHBr$_3$: $^1$H-NMR (600 MHz, CDCl$_3$): δ 6.71 [s]. $^{13}$C-NMR (600 MHz, CDCl$_3$): δ 9.73. GC-MS: $t_r$=5.73 min, % area=83%, m/z (rel. int %): 251 (14)[M$^+$], 173(100), 91(17), 80(15). C$_2$Br$_4$: $^{13}$C-NMR {$^1$H} (600 MHz, CDCl$_3$): δ 92.3. GC-MS: $t_r$=8.75 min, % area=17%, m/z (rel. int %): 344(100)[M$^+$], 263(72), 184 (55), 103(19), 91(8), 79(17).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

1. A. L. Horvath. (1982) Halogenated hydrocarbons: solubility-miscibility with water. New York: M. Dekker.
2. Parsons, F., et al. (1984) Transformation of tetrachloroethylene in micro-organisms and groundwater. *J. Am. Water. Work. Assoc.* 76, 56-60.
3. Marx, J. L. (1974) Drinking water: another source of carcinogens? *Science.* 186, 809-811.
4. Wang, T. C., et al. (1985) Impact of trichloroethylene contaminated ground water discharged to the Main Canal and Indian River Lagoon. *Bull. Environ. Contam. Toxicol.* 34, 578-586.
5. U.S. Pat. No. 1,627,881. Bellone, A. F. (1927) Process for the reduction of halogenated hydrocarbons.
6. Wang, T. C. et al. (1990) Reduction of halogenated hydrocarbons with magnesium hydrolysis process. *Bull. Environ. Contam. Toxicol.* 45, 149-156.
7. The oxidation of 1H by elemental sulfur ($S_8$) has been examined previously but requires elevated temperatures (150° C.): Denk, M. K., Gupta, S., Brownie, J., Tajammul, S., Lough, A. J. C—H activation with elemental sulfur: synthesis of cyclic thioureas from formaldehyde aminals and $S_8$. *Chem. Eur. J.* 7, 4477-4486 (2001).
8. Denk, M. K., Hezarkhani, A., Zheng, F. Steric and Electronic Effects in the Dimerization of Wanzlick Carbenes: The Alkyl Effect. *Eur. J. Inorg. Chem.* 3527-3530 (2007).
9. To the best of the Applicant's knowledge the only previously reported reduction of a halogenated hydrocarbon by an imidazolidine seems to be the reaction of 1,3-diphenyl-imidazolidine with $CCl_4$: Rabe, E., Wanzlick, H.-W. Dehydrierung von 1,3-Diaryl-imidazolidinen mit Tetrachlor-kohlenstoff. *Liebigs Ann. Chem.* 40-44 (1973).

The invention claimed is:

1. A method of reducing one or more halogenated compounds comprising contacting the one or more halogenated compounds with one or more compounds of Formula (I) under conditions for the reduction of the one or more halogenated compounds, wherein the compound of Formula (I) is:

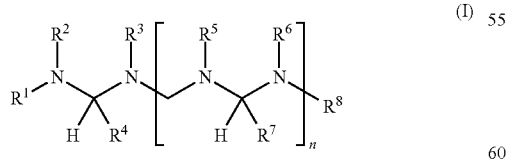

wherein
$R^1$, $R^2$, $R^3$ and $R^8$ and each $R^5$ and $R^6$ are independently selected from $C_{1-6}$alkyl, $C_{3-10}$cycloalkyl, $C_{6-10}$aryl and $C_{5-10}$heteroaryl; or
$R^2$ and $R^3$ and/or each $R^5$ and $R^6$, together with the nitrogen atoms to which they are attached, form a 5-7 membered carbocycle wherein 1 or 2 carbons are optionally replaced with $NR^9$;
$R^4$ and each $R^7$ are independently selected from H and $C_{1-6}$alkyl;
each $R^9$ is independently selected from $C_{1-6}$alkyl, $C_{3-10}$cycloalkyl, $C_{6-10}$aryl and $C_{5-10}$heteroaryl; and
n is 0-18, and
wherein the one or more halogenated compounds, is not $CA_4$, wherein A is chloro.

2. The method of claim 1, wherein the compound of Formula (I) is a compound of Formula (I)(i):

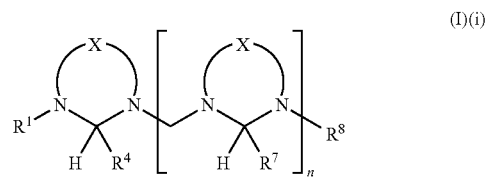

wherein
each X is independently $C_{2-4}$alkylene, wherein 1 or 2 of the $CH_2$ groups is optionally replaced with $NR^9$;
$R^1$ and $R^8$ and each $R^9$ are independently selected from $C_{1-6}$alkyl, $C_{3-10}$cycloalkyl, $C_{6-10}$aryl and $C_{5-10}$heteroaryl;
$R^4$ and each $R^7$ are independently selected from H and $C_{1-6}$alkyl; and
n is 0-18.

3. The method of claim 2, wherein n is 1-18.

4. The method of claim 2, wherein n is 0.

5. The method of claim 4, wherein the compound of Formula (I)(i) is a compound of Formula (I)(i)(a), (I)(i)(b) or (I)(i)(c):

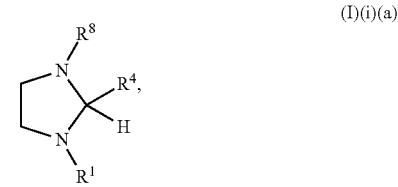

wherein $R^1$, $R^4$ and $R^8$ are as defined in claim 1.

6. The method of claim 5, wherein the compound of Formula (I)(i)(a) is:

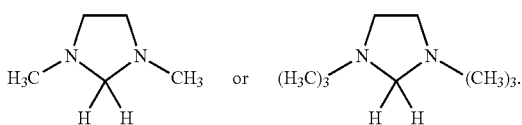

7. The method of claim 1, wherein the conditions for the reduction of the one or more halogenated compounds comprise treating the one or more halogenated compounds with an excess of one or more compounds of Formula (I) at temperatures and for a time sufficient for the reduction of the one or more halogenated compounds.

8. The method of claim 7, wherein the reduction of the one or more halogenated compounds results in the concomitant formation of halogen salts of the compound of Formula (I) as by-products.

9. The method of claim 8, wherein the salt of the compound of Formula (I) is:

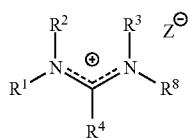

wherein
$R^1$, $R^2$, $R^3$ and $R^8$ are independently selected from $C_{1-6}$alkyl, $C_{3-10}$cycloalkyl, $C_{6-10}$aryl and heteroaryl; or $R^2$ and $R^3$, together with the nitrogen atoms to which they are attached, form a 5-7 membered carbocycle wherein 1 or 2 carbons are optionally replaced with $NR^9$;
$R^4$ is selected from H and $C_{1-6}$alkyl;
$R^9$ is independently selected from $C_{1-6}$alkyl, $C_{3-10}$cycloalkyl, $C_{6-10}$aryl and heteroaryl; and
Z is a halogen counteranion.

10. The method of claim 1, wherein the compounds of Formula (I) are used in catalytic amounts in the presence of other reducing agents.

11. The method of claim 10, wherein the other reducing agent is sodium dithionite.

12. The method of claim 10, wherein the catalytic amount of the compound of Formula (I) is generated in situ from the reduction of a halogen salt of the compound of Formula (I).

13. The method of claim 1, wherein the one or more halogenated compounds are selected from halogenated arenes and linear and/or cyclic halogenated alkanes.

14. The method of claim 13, wherein one or more halogenated compounds are selected from 2-bromo-2-chloro-1,1,1-trifluoroethane, 1,2-dibromoethane, 1,2-dichloroethane, $CH_3Br$, $CH_2Br_2$, $CHBr_3$, $CHCl_3$, $C_2H_2I_2$, 1,2-dibromocyclohexane, 1-bromoadamantane 4,4'-dichlorodiphenyltrichloroethane (DDT), 1,3,5-tribromobenzene, 1,3-dibromobenzene, bromobenzene, 1,4-diiodobenzene and iodobenzene.

15. The method of claim 1, wherein the one or more halogenated compounds are linear cyclic halogenated alkanes comprising a C—Br bond and one or more C—Cl and/or C—F bonds and the method comprises the selective reduction of the C—Br bond.

16. The method of claim 1, wherein the one or more halogenated compounds are comprised in soil and the reduction of the one or more halogenated compounds decontaminates the soil of halogenated compounds.

17. The method of claim 1, wherein the one or more halogenated compounds are comprised in a chemical warfare agent and the reduction of the one or more halogenated compounds degrades or detoxifies the chemical warfare agent.

18. A method of recovering precious metals, the method comprising:
a) adsorbing one or more compounds of Formula (I) as defined in claim 1 onto a support material;
b) contacting a solution comprising precious metals with the adsorbed one or more compounds of Formula (I) under conditions for the reduction of the precious metals; and
c) removing the adsorbed precious metals from the support material.

19. The method of claim 18, wherein the support material is selected from highly dispersive silicic acid (HDS), activated charcoal and diatomaceous earth (kieselguhr).

20. The method of claim 18, wherein the adsorbed precious metals are removed from the support material using chemical reagents selected from oxidants, cyanides, phosphines, chelating agents and thiosulfates.

* * * * *

UNITED STATES PATENT AND TRADEMARK OFFICE
CERTIFICATE OF CORRECTION

PATENT NO. : 9,744,392 B1
APPLICATION NO. : 15/440077
DATED : August 29, 2017
INVENTOR(S) : Michael K. Denk, Nicholas Milutinovic and Katherine Marczenko It is certified that error appears in the above-identified patent and that said Letters Patent is hereby corrected as shown below:

In the Claims

1. Column 26, Line 8, Claim 14 "1-bromoadamantane" should read --1-bromoadamantane,--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*